United States Patent [19]

Sturm et al.

[11] 4,406,895
[45] Sep. 27, 1983

[54] BASE-SUBSTITUTED ANTHRANILIC ACIDS, A PROCESS FOR THEIR PREPARATION AND THEIR USE

[75] Inventors: Karl Sturm, Heidesheim; Roman Muschaweck, Frankfurt am Main; Max Hropot, Flörsheim am Main, all of Fed. Rep. of Germany

[73] Assignee: Hoechst Aktiengesellschaft, Frankfurt am Main, Fed. Rep. of Germany

[21] Appl. No.: 341,006

[22] Filed: Jan. 20, 1982

[30] Foreign Application Priority Data

Jan. 22, 1981 [DE] Fed. Rep. of Germany ....... 3101960

[51] Int. Cl.³ .................. A61K 31/625; A61K 31/63; C07D 231/42; C07C 143/78
[52] U.S. Cl. .................................. 424/229; 424/228; 260/239.6; 260/397.7 R
[58] Field of Search .................... 260/397.7 R, 239.6; 424/228, 229

[56] References Cited

U.S. PATENT DOCUMENTS

| | | | |
|---|---|---|---|
| 3,346,568 | 10/1967 | Schmidt et al. | 260/397.7 R |
| 3,444,177 | 5/1969 | Schmidt et al. | 260/397.7 R |
| 3,532,792 | 10/1970 | Wilson | 260/397.7 R |
| 3,565,920 | 2/1971 | Werner | 260/397.7 R |
| 3,568,990 | 4/1972 | Werner | 260/397.7 R |
| 3,678,039 | 7/1972 | Werner | 260/397.7 R |
| 3,755,383 | 8/1973 | Feit et al. | 260/397.7 R |
| 3,758,522 | 9/1973 | Feit et al. | 260/397.7 R |
| 3,790,584 | 2/1974 | Feit et al. | 260/397.7 R |
| 3,914,219 | 10/1975 | Lerch et al. | 260/397.7 R |
| 4,001,284 | 1/1977 | Sturm | 260/397.7 R |

FOREIGN PATENT DOCUMENTS 884316 10/1971 Canada .
1484606 9/1977 United Kingdom .

*Primary Examiner*—A. Siegel
*Attorney, Agent, or Firm*—Curtis, Morris & Safford

[57] ABSTRACT

The invention relates to base-substituted anthranilic acids of the formula I

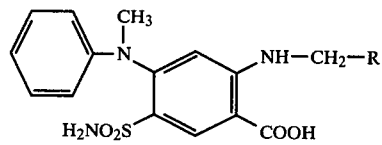

in which R denotes furyl, thienyl or phenyl, and to physiologically acceptable salts thereof, and also to a process for their preparation, to an agent containing these and to their use as medicaments.

5 Claims, No Drawings

BASE-SUBSTITUTED ANTHRANILIC ACIDS, A PROCESS FOR THEIR PREPARATION AND THEIR USE

The invention relates to compounds of the formula I, which can be classified as belonging to the group of 5-sulfamoylanthranilic acids, and to physiologically acceptable salts thereof.

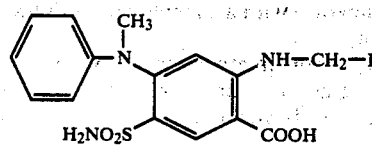

In the formula I, R denotes furyl, thienyl or phenyl, preferably 2-furyl or 2-thienyl.

Cations of the salts of I claimed which are suitable for a therapeutic use are, in particular, the sodium, potassium or ammonium ion or substituted ammonium ions. Salts formed from I and a basic medicament, such as antihypertensive agents, β blockers or potassium-retaining substances, are also of particular importance.

The invention also relates to a process for the preparation of compounds of the formula I, which comprises hydrolyzing a nitrile of the formula II

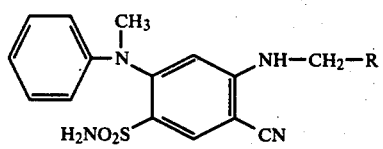

to give the corresponding carboxylic acid. The hydrolysis is preferably carried out in an alkaline medium, and, if appropriate, it can also be conducted via the intermediate stage of an amidrazone, amidine, iminoether, amide or thioamide which are prepared from the nitrile in a customary manner.

Direct hydrolysis of compounds of the formula II which is carried out under reflux by means of an excess of an aqueous sodium hydroxide or potassium hydroxide solution is the industrially preferred process. After the hydrolysis is complete, the final products are advantageously precipitated at pH 3–4 in the form of crystals of the free carboxylic acid and, after purification by means of recrystallization, then converted into the corresponding salts, if appropriate, by means of a calculated amount of an alkali metal hydroxide, an alkali metal carbonate or an amine.

In particular those salts are of pharmacological importance which are formed from compounds according to the invention and basic potassium-retaining compounds, such as, for example, amiloride or triamterene or basic antihypertensive agents, such as, for example, clonidine, dihydralazine or β blockers. In these salts the pharmacological properties of both the components take effect.

The preparation of nitriles of the formula II which are used as a starting material has been described in a previous patent application No. P 30 41 812.3 (HOE 80/F 254).

Compounds according to the invention are salidiuretics of the furosemide type. By comparison with furosemide they are distinguished by a higher potency, improved absorbability and a uricosuric action component.

They are used for the treatment of cardiac, renal or hepatic edemas, ascites, edemas during pregnancy, edemas after burns and edemas after venous insufficiency or after thromboses. They are also used for the treatment of mild to moderate hypertension.

In the case of mammals or of man the administration is preferably carried out orally or intravenously, and a pure active compound dosage unit, relative to a normal weight adult patient, is between 1 and 50 mg. For an oral method of administration the active compounds are either used in a pure form or are mixed with additives customary for the purpose, such as carriers, stabilizers or inert diluents, and, by means of customary methods, are brought into suitable forms for administration, such as, for example, tablets, dragees or hard capsules. Examples of suitable inert carriers are magnesium carbonate, lactose and corn starch. This formulation may be in the form of a dry granular powder or a moist granular powder.

For intravenous administration the active compounds, preferably in the form of their physiologically acceptable alkali metal salts or ammonium salts, are dissolved in substances customary for this purpose. A preferred solvent is water, if appropriate with the addition of known buffer substances, solubilizers and stabilizers.

EXAMPLES

EXAMPLE 1

N-(2-Furylmethyl)-4-(N-methylanilino)-5-sulfamoylanthranilic acid 38.3 g of 2-furfurylamino-4-(N-methylanilino)-5-sulfamoylbenzonitrile (0.1 mole) were heated for 3 hours under reflux with 0.3 l of 2 N NaOH. The reaction solution was then adjusted to pH 8 by means of 2 N HCl, the solution was decolorized by means of active charcoal and the filtrate was then adjusted to pH 3.0 by means of 2 N HCl. After standing for one hour at room temperature the crystalline precipitate was filtered off with suction, washed thoroughly with water and dried in air. Yield: 28.0 g of the trihydrate (62% of theory), melting point 145° C. (with evolution of gas).

EXAMPLE 2

N-(2-Thienylmethyl)-4-(N-methylanilino)-5-sulfamoylanthranilic acid 39.9 g of 2-(2-thienylmethylamino)-4-(N-methylanilino)-5-sulfamoylbenzonitrile (0.1 mole) were heated for 3 hours under reflux with 0.3 l of 2 N NaOH and the final product was isolated as the trihydrate analogously to Example 1. Yield: 31.5 g (67% of theory), no sharp melting point (sintering occurred from 80° C. onwards), thin layer chromatography: single spot (silica gel, 10:1 methylene chloride/methanol, $R_f$ 0.73)

EXAMPLE 3

N-Benzyl-4-(4-methylanilino)-5-sulfamoylanthranilic acid 39.3 g of 2-benzylamino-4-(N-methylanilino)-5-sulfamoylbenzonitrile (0.1 mole) were hydrolyzed analogously to Example 1 by means of 0.3 l of NaOH and the filter-moist final product which precipitated at pH 3.0 was recrystallized from isopropanol. After drying on a steam bath, the compound still contained 1 mole equivalent of crystal isopropanol. Yield: 28.5 g (59% of theory), melting point 128° C. (with evolution of gas).

We claim:

1. A base-substituted anthranilic acid of the formula I

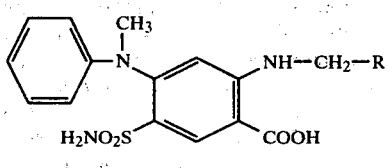

in which R denotes furyl, thienyl or phenyl, or a physiologically acceptable salt thereof.

2. The anthranilic acid as claimed in claim 1, in which R is 2-furyl or 2-thienyl.

3. The physiologically acceptable salt of anthranilic acid as claimed in claim 1 formed by a suitable basic potassium-containing compound or basic antihypertensive agent.

4. A pharmaceutical composition comprising a diuretically effective amount of a compound as defined in claim 1 in admixture with a suitable oral or intravenous inert excipient.

5. A method for the treatment of edemas or hypertension comprising administration of an effective amount of a compound as claimed in claim 1 as medicament.

* * * * *